United States Patent
Gao et al.

(10) Patent No.: US 12,171,687 B2
(45) Date of Patent: Dec. 24, 2024

(54) ITCH RELIEVING DEVICE

(71) Applicant: Zhongshan TLC Electronics Co., Ltd., Guangdong (CN)

(72) Inventors: Liyun Gao, Zhongshan (CN); Xiaofeng Zhang, Zhongshan (CN); Chadi Michael Diba, Zhongshan (CN)

(73) Assignee: ZHONGSHAN TLC ELECTRONICS CO., LTD., Guangdong (CN)

( * ) Notice: Subject to any disclaimer, the term of this patent is extended or adjusted under 35 U.S.C. 154(b) by 301 days.

(21) Appl. No.: 17/708,908

(22) Filed: Mar. 30, 2022

(65) Prior Publication Data

US 2023/0233363 A1 Jul. 27, 2023

(51) Int. Cl.
*A61F 7/00* (2006.01)
*A61F 7/02* (2006.01)

(52) U.S. Cl.
CPC ...... *A61F 7/007* (2013.01); *A61F 2007/0052* (2013.01); *A61F 2007/0087* (2013.01); *A61F 2007/0095* (2013.01); *A61F 2007/0284* (2013.01); *A61F 2007/0295* (2013.01)

(58) Field of Classification Search
CPC .............. A61F 2007/0052; A61F 7/007; A61F 2007/0087; A61F 2007/0093; A61F 2007/0095; A61F 2007/0284; A61F 2007/0295
See application file for complete search history.

(56) References Cited

U.S. PATENT DOCUMENTS

| | | | | |
|---|---|---|---|---|
| 6,312,397 | B1* | 11/2001 | Gebhard | A61F 7/007 601/15 |
| 2004/0127962 | A1* | 7/2004 | Li | A61F 7/007 607/96 |
| 2010/0179623 | A1* | 7/2010 | Hofer | A61F 7/007 607/96 |
| 2019/0201072 | A1* | 7/2019 | Shiraishi | A61N 1/20 |
| 2019/0290477 | A1* | 9/2019 | Bünger | A61P 43/00 |
| 2019/0290531 | A1* | 9/2019 | Bosma | A61H 7/00 |
| 2021/0236327 | A1* | 8/2021 | Bünger Von Wurmb | H04W 4/70 |
| 2021/0322205 | A1* | 10/2021 | Bünger Von Wurmb | A61F 7/007 |
| 2022/0142813 | A1* | 5/2022 | Bünger Von Wurmb | A61F 7/08 |

* cited by examiner

*Primary Examiner* — Kaitlyn E Smith
*Assistant Examiner* — Bradford C. Blaise
(74) *Attorney, Agent, or Firm* — Porter Wright Morris & Arthur LLP

(57) ABSTRACT

An itch relieving device is disclosed, including a shell, a heating element, a first touch sensing module, a control module and a gear input module. The first touch sensing module is configured for touching a human body to generate a human body sensing signal, the control module is electrically connected with the heating element to control the heating element to be switched on or off according to the human body sensing signal, the gear input module is configured for acquiring a control action to generate a pulse signal, the control module is provided with a storage unit, the control module is electrically connected with the gear input module to change a heating gear according to the pulse signal, the control module records the current heating gear through the storage unit, and the control module controls a heating power of the heating element according to the current heating gear.

8 Claims, 4 Drawing Sheets

ITCH RELIEVING DEVICE

CROSS-REFERENCE TO RELATED APPLICATIONS

This application is based on and claims the benefit of priority from Chinese Patent Application No. 2022201917075, filed on 24 Jan. 2022, the entirety of which is incorporated by reference herein.

TECHNICAL FIELD

The disclosure relates to the technical field of appliances, and more particularly, to an itch relieving device.

BACKGROUND

An existing itch relieving device may be used to touch a red and itchy position of a human body and relieve the itch of the user by heating. However, on-off statuses of a heating element of the former itch relieving device are controlled and switched by a key switch. If the itch relieving device is placed in a pocket, the key switch may be accidentally touched, which may cause damage to clothes.

Later, some manufacturers install a human body contact sensor on the itch relieving device, and the heating element is only allowed to be switched on when the human body contact sensor touches the human body. However, a heating power of the heating element is constant. For different red and itchy symptoms, the heating element needs to be operated at a heating temperature to produce a corresponding itch relieving effect. However, the control of the heating temperature of the heating element can be switched by a gear knob, but the gear knob needs to occupy a certain layout space. Meanwhile, the operation experience of the gear knob is troublesome. If other switching methods are adopted, it is generally necessary to control the heating element during operation of the heating element, so the heating temperature can only be switched when the human body contact sensor touches the human body, which is not easy to operate and has poor experience.

SUMMARY

The disclosure aims at solving at least one of the technical problems in the prior art. Therefore, the disclosure proposes an itch relieving device, which can change a heating power of a heating element, meet itch relieving needs of users, and is simple and convenient to operate.

An itch relieving device according to an embodiment in a first aspect of the disclosure includes: a shell; a heating element arranged in the shell; a first touch sensing module arranged on the shell, wherein the first touch sensing module is configured for touching a human body to generate a human body sensing signal; a control module arranged in the shell and electrically connected with the heating element and the first touch sensing module respectively to control the heating element to be switched on or off according to the human body sensing signal; and a gear input module arranged on the housing, wherein the gear input module is configured for acquiring a control action to generate a pulse signal, the control module is provided with a storage unit; the control module is electrically connected with the gear input module to change a heating gear according to the pulse signal, and the control module is configured for recording a current heating gear through the storage unit and controlling a heating power of the heating element according to the current heating gear.

The itch relieving device according to the embodiment of the disclosure at least has the following beneficial effects.

According to the itch relieving device of the disclosure, the user can control the gear input module, the gear input module forms the pulse signal input to the control module, the control module changes the heating gear according to the pulse signal, and the storage unit records the current heating gear. The control module changes the heating gear according to the pulse signal on the basis of the current heating gear recorded by the storage unit each time, so the changing of the heating gear has nothing to do with operating status of the heating element 200. When the first touch sensing module contacts the human body to generate the human body sensing signal, the control module can control the heating element to be switched on or off according to the human body sensing signal, and control the heating power of the heating element according to the current heating gear recorded by the storage unit. This design can change the heating power of the heating element, meet the itch relieving demand of the user, and is simple and convenient to operate.

According to some embodiments of the disclosure, the shell is provided with a contact part, and the heating element and the first touch sensing module are both arranged on the contact part.

According to some embodiments of the disclosure, the first touch sensing module is annular, and the first touch sensing module is arranged around the heating element.

According to some embodiments of the disclosure, the first touch sensing module is one or more of a capacitance sensor, a pressure sensor, a temperature sensor or a bioelectrical impedance sensor.

According to some embodiments of the disclosure, the gear input module includes a second touch sensing module, and the second touch sensing module is configured for sensing the control action by touching of the human body to generate the pulse signal.

According to some embodiments of the disclosure, the storage unit is an adding register unit, an input end of the adding register unit is connected with the gear input module so as to be triggered by the pulse signal to accumulate trigger times information, and the control module is connected with an output end of the adding register unit to change the heating gear according to the trigger times information.

According to some embodiments of the disclosure, the itch relieving device further includes a first switch module arranged on the shell, wherein the first switch module is connected with the control module to form at least part of a first power supply branch for accessing a power supply, and the first switch module is connected with the heating element to form at least part of a second power supply branch for accessing the power supply.

According to some embodiments of the disclosure, the itch relieving device further includes a second switch module, wherein the second switch module, the heating element and the first switch module are connected to form a second power supply branch, and the control module is connected with a controlled end of the second switch module to adjust the heating power of the heating element by controlling an operating current of the second power supply branch.

According to some embodiments of the disclosure, the control module is provided with a timing unit configured for providing a timing signal, and the control module is configured for controlling the heating element to operate intermittently according to the timing signal.

According to some embodiments of the disclosure, the itch relieving device further includes a temperature detection module, wherein the temperature detection module is configured for detecting a heating temperature of the heating element, and the control module is electrically connected with the temperature detection module.

The additional aspects and advantages of the disclosure will be partially given in the following description, and will partially become obvious from the following description, or learned through the practice of the disclosure.

BRIEF DESCRIPTION OF DRAWINGS

The above and/or additional aspects and advantages of the disclosure will be more apparent from the following description of the embodiments in conjunction with the accompanying drawings, wherein.

Figure 1:
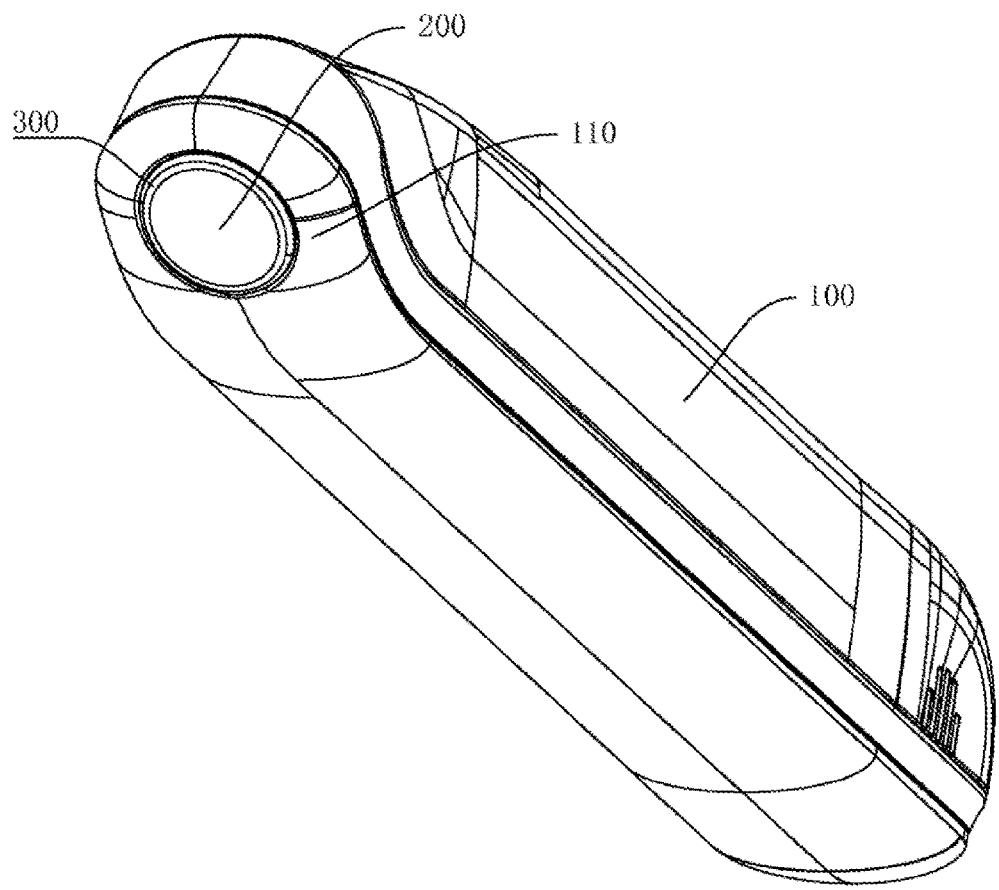
FIG. 1 is a schematic diagram from one angle of an itch relieving device according to an embodiment of the disclosure.

Reference numerals: 100 refers to shell, 110 refers to contact part, 200 refers to heating element, 300 refers to first touch sensing module, 400 refers to control module, 410 refers to storage unit, 420 refers to timing unit, 430 refers to power modulation module, 500 refers to gear input module, 600 refers to first switch module, 700 refers to second switch module, 800 refers to prompting module, and 900 refers to temperature detection module.

DETAILED DESCRIPTION

The embodiments of the disclosure will be described in detail hereinafter. Examples of the embodiments are shown in the accompanying drawings. The same or similar reference numerals throughout the drawings denote the same or similar elements or elements having the same or similar functions. The embodiments described below with reference to the accompanying drawings are exemplary and are only intended to explain the disclosure, but should not be construed as limiting the disclosure.

In the description of the disclosure, it should be understood that the orientations or positional relationships relating to orientation descriptions indicated by the terms such as "upper", "lower", "front", "rear", "left", "right", "vertical", "horizontal", "top", "bottom", "inner", "outer" and the like, refer to the orientations or positional relationships shown in the accompanying drawings, which are only intended to facilitate describing the disclosure and simplifying the description, and do not indicate or imply that the indicated devices or elements must have a specific orientation, be constructed and operated in a specific orientation, and therefore cannot be understood as a limitation of the disclosure.

In the description of the disclosure, "several" means one or more, "a plurality of" means more than two, "greater than a number", "less than a number", "exceed a number" and the like indicate that the number is excluded, and "above a number", "below a number", "within a number", and the like indicate that the number is included. "First" and "second" are only used to distinguish between technical features but cannot be used to indicate or imply relative importance or implicitly specify a quantity of indicated technical features or implicitly specify a sequential relationship of indicated technical features.

In the description of the disclosure, it should be noted that unless expressly stipulated and defined otherwise, terms such as "installation", "connected" and "connection", etc., should understood broadly, for example, the connection may be fixed connection, or detachable connection or integral connection; may be mechanical connection, and may also be electrical connection; and may be direct connection, may also be indirect connection through an intermediate medium, and may also be internal communication of two elements. The specific meaning of the above terms in the disclosure can be understood in a specific case by those skilled in the art.

As shown in FIGS. 1 to 7, an itch relieving device according to an embodiment in a first aspect of the disclosure includes a shell 100, a heating element 200, a first touch sensing module 300, a control module 400 and a gear input module 500. The first touch sensing module 300, the heating element 200 and the gear input module 500 are arranged on the shell 100, the first touch sensing module 300 is configured for touching a human body to generate a human body sensing signal, the control module 400 is arranged in the shell 100 and electrically connected with the heating element 200 and the first touch sensing module 300 respectively to control the heating element 200 to be switched on or off according to the human body sensing signal, the gear input module 500 is configured for acquiring a control action to generate a pulse signal, the control module 400 is provided with a storage unit 410, the control module 400 is electrically connected with the gear input module 500 to change a heating gear according to the pulse signal, the control module 400 records the current heating gear through the storage unit 410, and the control module 400 controls a heating power of the heating element 200 according to the current heating gear.

The control module 400 may be composed of a CPU, a MCU and other processing chips with auxiliary circuits, and the heating element 200 may be a semiconductor heating piece or a ceramic heating piece, and the like.

The shell 100 may be rod-shaped, and the heating element 200 may be arranged at an end portion of the shell 100. A user may hold the shell 100 for convenient use.

It should be noted that the above-mentioned heating gear is only used to illustrate the difference of heating degrees, and the specific adjustment of the heating power may be stepping control or stepless control.

According to the itch relieving device of the disclosure, the user can control the gear input module 500, the gear input module 500 forms the pulse signal input to the control module 400, the control module 400 changes the heating gear according to the pulse signal, and the storage unit 410 records the current heating gear. The control module 400 changes the heating gear according to the pulse signal on the basis of the current heating gear recorded by the storage unit 410 each time, so the changing of the heating gear has nothing to do with operating status of the heating element 200. When the first touch sensing module 300 contacts the human body to generate the human body sensing signal, the control module 400 can control the heating element 200 to be switched on or off according to the human body sensing signal, and control the heating power of the heating element 200 according to the current heating gear recorded by the storage unit 410. This design can change the heating power of the heating element 200, meet the itch relieving demand of the user, and is simple and convenient to operate.

Figure 2:
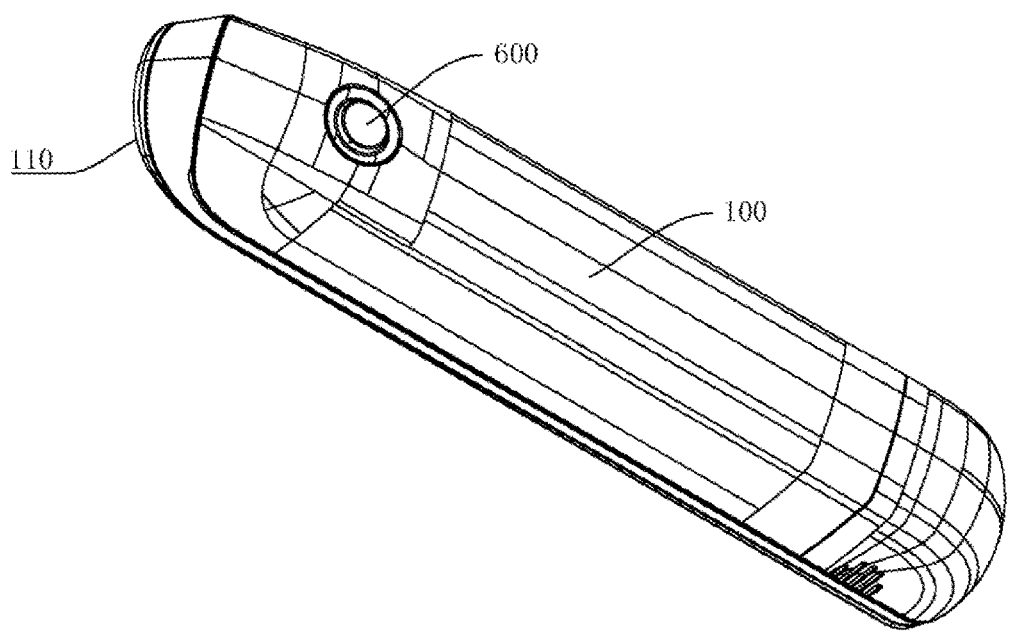
FIG. 2 is a schematic diagram from another angle of the itch relieving device according to an embodiment of the disclosure.

In some embodiments of the disclosure, as shown in FIGS. 1 and 2, the shell 100 is provided with a contact part 110, and both the heating element 200 and the first touch sensing module 300 are arranged on the contact part 110. When the heating element 200 touches a red and itchy position of the human body, the first touch sensing module 300 can also touch a position near the red and itchy position, so that the control module 400 can control the operation of the heating element 200, which is convenient to use.

Specifically, the contact part 110 may be located on a plane or inclined plane at the end portion of the rod-shaped shell 100, and the contact part 110 and the shell 100 are of an integrated structure.

Of course, in some embodiments of the disclosure, the first touch sensing module 300 may also be located at different positions of the shell 100 from the heating element 200, and the user touches the first touch sensing module 300 with a finger, thus driving the heating element 200 to operate.

In the embodiment where both the heating element 200 and the first touch sensing module 300 are arranged on the contact part 110, the first touch sensing module 300 is annular, and the first touch sensing module 300 is arranged around the heating element 200, so that when the heating element 200 contacts the human body, the annular first touch sensing module 300 can be more easily contacted with the human body, so that the heating element 200 can keep operating stably.

In some embodiments of the disclosure, the first touch sensing module 300 is one or more of a capacitance sensor, a pressure sensor, a temperature sensor or a bioelectrical impedance sensor.

Movement of charges in the capacitance sensor can be induced after the capacitance sensor contacts the human body, thereby it can be judged whether the human body is contacted. The pressure sensor judges whether the human body is contacted according to a pressure change caused by abutting against the human body. The temperature sensor judges whether the human body is contacted according to a temperature change after contacting the human body. The bioelectrical impedance sensor judges whether the human body is contacted according to a resistance change caused by contacting the human body.

In some embodiments of the disclosure, the gear input module 500 includes a second touch sensing module, the second touch sensing module is configured for sensing the control action by touching of the human body to generate the pulse signal. Changing the gears by sensing a touch action makes the operation simpler and more convenient.

Specifically, the second touch sensing module may also be one or more of a capacitance sensor, a pressure sensor, a temperature sensor or a bioelectrical impedance sensor.

In some embodiments of the disclosure, the storage unit 410 is an adding register unit, an input end of the adding register unit is connected with the gear input module 500 so as to be triggered by the pulse signal to accumulate trigger times information, and the control module 400 is connected with an output end of the adding register unit to change the heating gear according to the trigger times information. The gear can be stably adjusted by adding 1 through the adding register unit, for example, the heating power of the heating element 200 is divided into three levels. Every time triggered by the gear input module 500, an output of the adding register unit is added by 1, and when the output of the adding register unit is level 3, the heating power returns to level 1 if the output is added by 1 again.

Specifically, the adding register may be composed of an adder and a register. A first input end of the adder is connected with the gear input module 500, a second input end of the adder is connected with an output end of the register, the adder adds signals input from the first input end and the second input end, and an output end of the adder is respectively output to the control module 400 and the input end of the register.

In some embodiments of the disclosure, the storage unit 410 may also be a memory in the control module 400, which can record the heating gear, and the heating element can be controlled based on the current heating gear.

Figure 3:
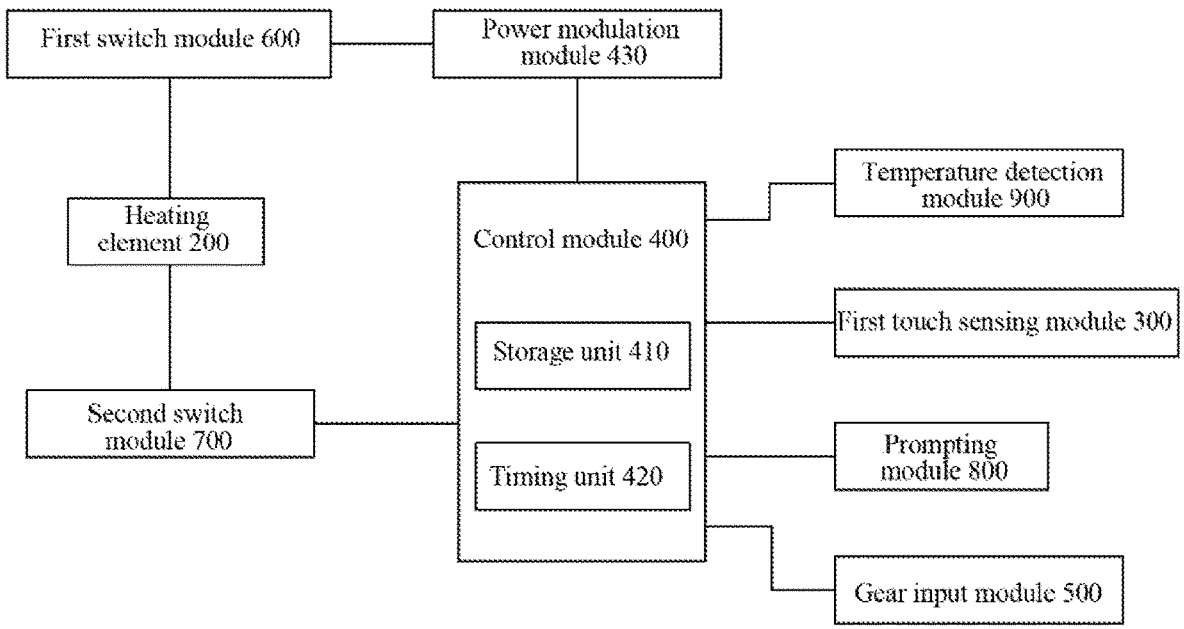
FIG. 3 is a schematic structural block diagram of the itch relieving device according to an embodiment of the disclosure.
Figure 4:
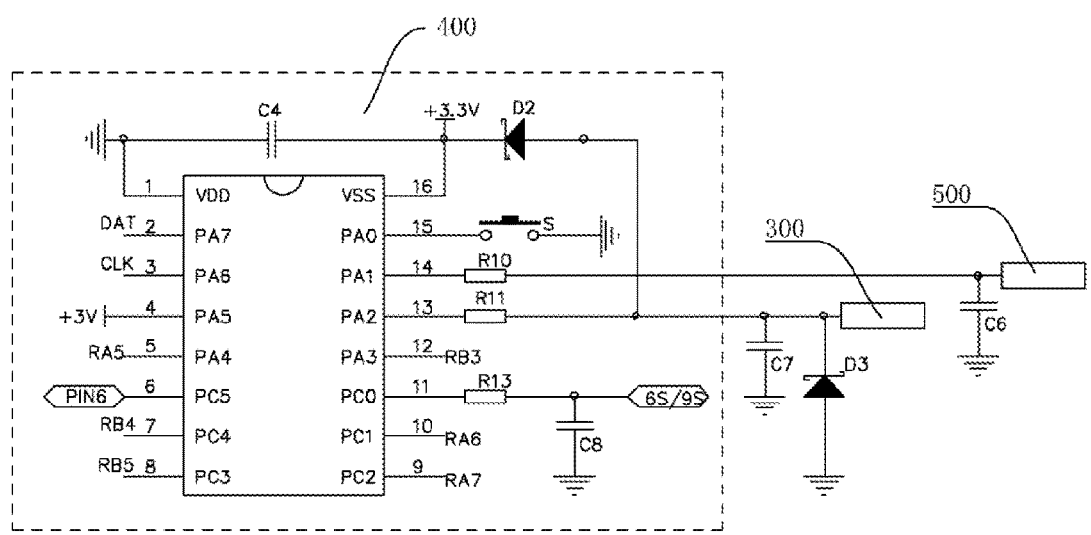
FIG. 4 is a schematic circuit diagram of a control module.
Figure 5:
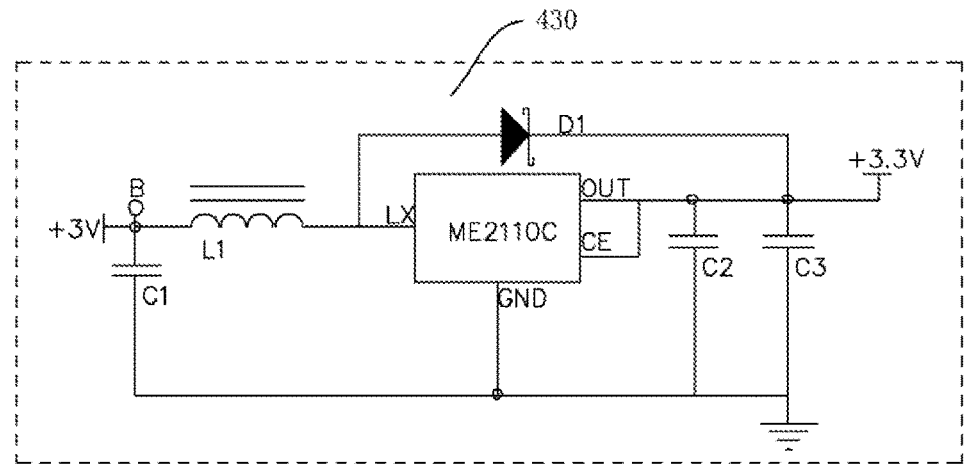
FIG. 5 is a schematic circuit diagram of a power modulation module.

In some embodiments of the disclosure, as shown in FIG. 3, the itch relieving device further includes a first switch module 600 arranged in the shell 100, wherein the first switch module 600 is connected with the control module 400 to form at least part of a first power supply branch for accessing a power supply, and the first switch module 600 is connected with the heating element 200 to form at least part of a second power supply branch for accessing the power supply. The first switch module 600 may be used as a master switch of the itch relieving device. Arrangement of the first power supply branch and the second power supply branch enables lines for supplying power to the heating element 200 and the control module 400 to be separated and not influence each other. When the heating element 200 is not supplied with power, the control module 400 can still be supplied with power, so that a switching function of the heating gear can still be normally realized, and the on-off can be controlled uniformly by the first switch module 600. Specifically, the first switch module 600 may be a key switch, a touch switch and the like arranged on the shell 100.

In some embodiments of the disclosure, the control module 400 can also detect a pressing status of the first switch module 600, and the pulse signal formed by the pressing status of the first switch module 600 can also trigger the switching of the heating gear.

Specifically, the shell 100 is provided with a battery compartment for holding a storage battery. The storage battery serves as the power supply, which can supply power to the control module 400 and the heating element 200 respectively. Specifically, the storage battery may be a No. 5 alkaline battery. A power modulation module 430 is further provided in the first power supply branch. Specifically, the power modulation module 430 may be composed of a voltage regulating chip and an auxiliary circuit. The power modulation module 430 modulates a voltage output by the power supply, so as to modulate an appropriate voltage to supply power to the control module 400.

Figure 7:
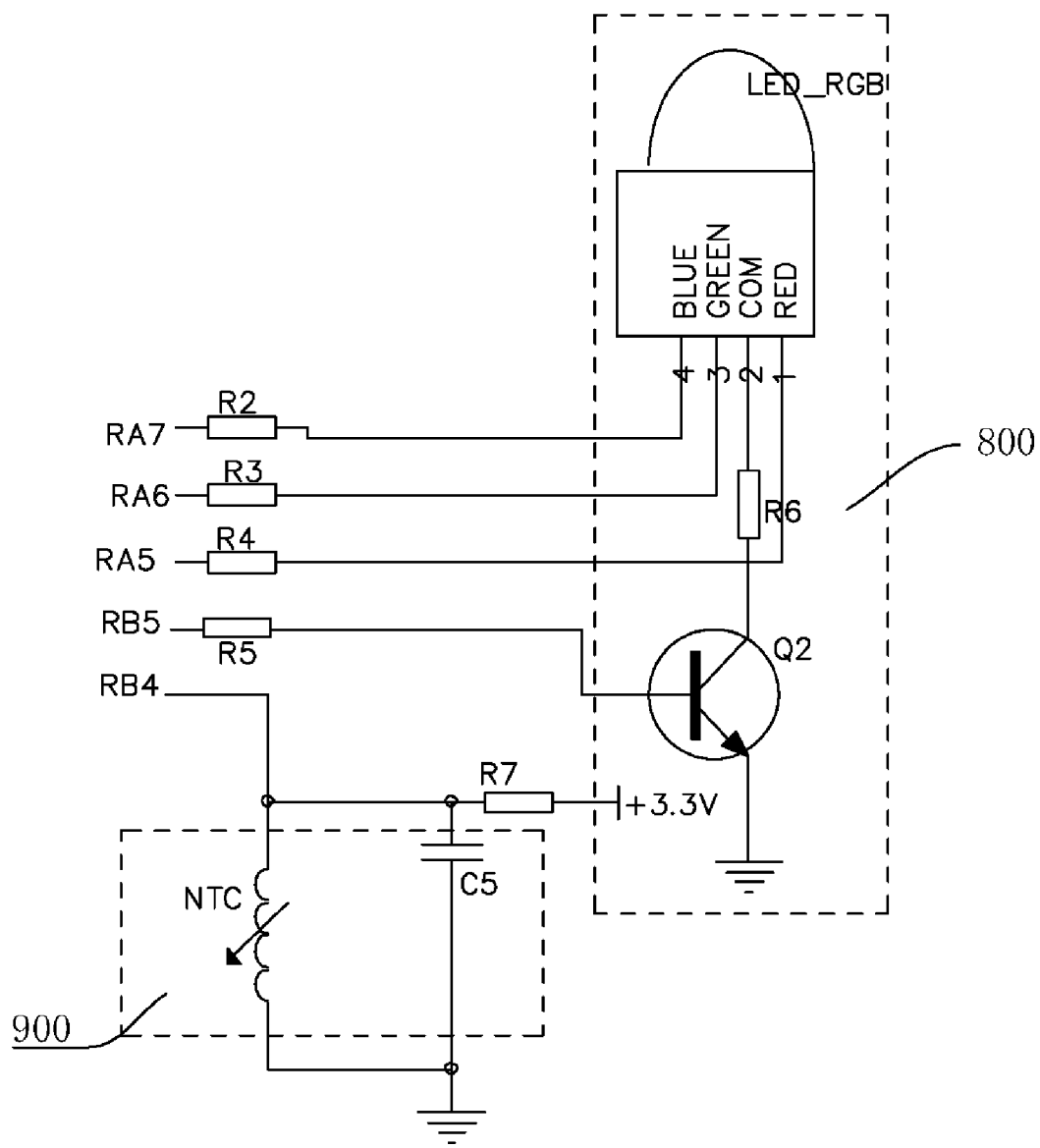
FIG. 7 is a schematic circuit diagram of a prompting module and a temperature detection module.

In some embodiments of the disclosure, as shown in FIG. 7, the shell 100 may also be provided with a prompting module 800. The prompting module 800 may be an indicator light or a loud speaker, and the control module 400 can display the current heating gear through the prompting module 800. For example, when the prompting module 800 is an indicator light, the current heating gear can be displayed through different luminous colors.

Figure 6:
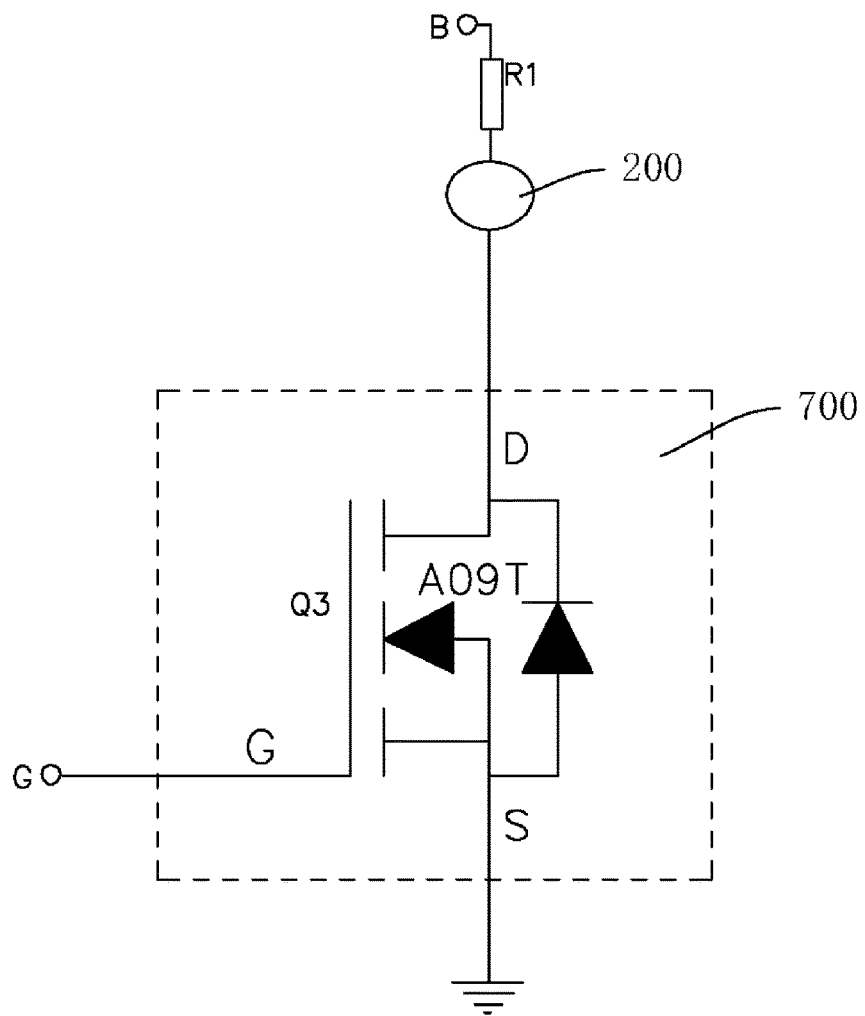
FIG. 6 is a schematic circuit diagram of a second power supply branch.

In some embodiments of the disclosure, as shown in FIG. 6, the itch relieving device further includes a second switch module 700 arranged in the shell 100, wherein the second switch module 700, the heating element 200 and the first switch module 600 are connected to form a second power supply branch, and the control module 400 is connected with a controlled end of the second switch module 700 to adjust the heating power of the heating element 200 by controlling an operating current of the second power supply branch.

The second switch module 700 may be any one of a triode, a MOS transistor, a silicon controlled rectifier and an IBGT. The control module 400 may input PWM signals to adjust the operating current of the heating element 200 by controlling the on-off of the second switch module 700, so as to control the heating power of the heating element 200 to adjust the heating temperature.

In some embodiments of the disclosure, the control module 400 is provided with a timing unit 420. The timing unit is configured for providing a timing signal, and the control module 400 controls the heating element 200 to operate intermittently according to the timing signal.

Specifically, the timing unit 420 may be composed of a time-based control circuit or a timing program. The control module 400 can control the heating element 200 by setting a time threshold and the timing signal. For example, the control module 400 can control the heating element 200 to start running for 6 seconds to 9 seconds, and then stop or restart running after stopping for 6 seconds and operate intermittently with this logic, so that the red and itchy position can be heated for a period of time and then stopped to prevent skin damage caused by overheating.

In some embodiments of the disclosure, as shown in FIG. 7, the itch relieving device further includes a temperature detection module 900, wherein the temperature detection module 900 is configured for detecting a heating temperature of the heating element 200, and the control module 400 is electrically connected with the temperature detection module 900. The temperature detection module 900 detects the heating temperature of the heating element 200, and the control module 400 controls the operation of the heating element 200 according to the temperature detection information, so as to prevent skin damage caused by overheating of the heating element 200 and improve safety performance. Specifically, the temperature detection module 900 may be selected from conventional temperature sensors.

The technical features of the above embodiments can be combined in any way. In order to simplify the description, not all the possible combinations of the technical features of the above embodiments are described. However, as long as there is no contradiction in the combinations of these technical features, they should be considered as falling within the scope recorded in this specification.

Although the embodiments of the disclosure have been shown and described, those of ordinary skills in the art should understand that: various changes, amendments, substitutions and modifications can be made to these embodiments without departing from the principles and purposes of the disclosure, and the scope of the disclosure is limited by the claims and equivalents thereof

What is claimed is:

1. An itch relieving device, comprising:
   a shell;
   a heating element arranged on the shell;
   a first touch sensing module arranged on the shell, wherein the first touch sensing module is configured for touching a human body to generate a human body sensing signal;
   a control module arranged in the shell and electrically connected with the heating element and the first touch sensing module respectively to control the heating element to be switched on or off according to the human body sensing signal;
   a gear input module arranged on the shell, wherein the gear input module is configured for acquiring a control action to generate a pulse signal, the control module is provided with a storage unit; the control module is electrically connected with the gear input module to change a heating gear according to the pulse signal, and the control module is configured for recording a current heating gear through the storage unit and controlling a heating power of the heating element according to the current heating gear;
   a first switch module arranged on the shell, wherein the first switch module is connected with the control module to form at least part of a first power supply branch for accessing a power supply, and the first switch module is connected with the heating element to form at least part of a second power supply branch for accessing the power supply; and
   a second switch module, wherein the second switch module, the heating element and the first switch module are connected to form the second power supply branch, and the control module is connected with a controlled end of the second switch module to adjust the heating power of the heating element by controlling an operating current of the second power supply branch.

2. The itch relieving device of claim 1, wherein the shell is provided with a contact part, and the heating element and the first touch sensing module are both arranged on the contact part.

3. The itch relieving device of claim 2, wherein the first touch sensing module is annular, and the first touch sensing module is arranged around the heating element.

4. The itch relieving device of claim 1, wherein the first touch sensing module is one or more of a capacitance sensor, a pressure sensor, a temperature sensor or a bioelectrical impedance sensor.

5. The itch relieving device of claim 1, wherein the gear input module comprises a second touch sensing module, and the second touch sensing module is configured for sensing the control action by touching of the human body to generate the pulse signal.

6. The itch relieving device of claim 1, wherein the storage unit is an adding register unit, an input end of the adding register unit is connected with the gear input module so as to be triggered by the pulse signal to accumulate trigger times information, and the control module is connected with an output end of the adding register unit to change the heating gear according to the trigger times information.

7. The itch relieving device of claim 1, wherein the control module is provided with a timing unit configured for providing a timing signal, and the control module is configured for controlling the heating element to operate intermittently according to the timing signal.

8. The itch relieving device of claim 1, further comprising a temperature detection module, wherein the temperature detection module is configured for detecting a heating temperature of the heating element, and the control module is electrically connected with the temperature detection module.

* * * * *